United States Patent
Pomerantz

Patent Number: 5,774,055
Date of Patent: Jun. 30, 1998

[54] INFANT MONITORING DEVICE

[76] Inventor: David Pomerantz, 251 174th St., Apt. 504, Miami Beach, Fla. 33160

[21] Appl. No.: 871,832

[22] Filed: Jun. 9, 1997

[51] Int. Cl.⁶ .................................................. G08B 23/00
[52] U.S. Cl. ........................ 340/573; 340/573; 340/575; 340/689; 340/517; 340/524; 340/521
[58] Field of Search ............................... 340/573, 825.03, 340/825.57, 825.71, 517, 524, 521, 604, 575, 689; 455/128, 59, 61, 149

[56] References Cited

U.S. PATENT DOCUMENTS

| | | | |
|---|---|---|---|
| 3,831,586 | 8/1974 | Petit | 128/2 R |
| 4,348,562 | 9/1982 | Florin | 200/52 R |
| 4,617,525 | 10/1986 | Lloyd | 340/573 |
| 4,800,370 | 1/1989 | Vetecnik | 340/573 |
| 4,884,067 | 11/1989 | Nordholm et al. | 340/686 |
| 4,899,133 | 2/1990 | Bartlett | 340/573 |
| 4,938,476 | 7/1990 | Brunelle et al. | 272/93 |
| 4,972,177 | 11/1990 | Nolan | 340/573 |
| 5,038,137 | 8/1991 | Lloyd | 340/573 |
| 5,081,447 | 1/1992 | Echols | 340/573 |
| 5,168,264 | 12/1992 | Agustin | 340/573 |
| 5,241,300 | 8/1993 | Buschmann | 340/573 |
| 5,469,861 | 11/1995 | Piscopo et al. | 128/781 |

*Primary Examiner*—Jeffery A. Hofsass
*Assistant Examiner*—Toan N. Pham
*Attorney, Agent, or Firm*—Jack Lo

[57] ABSTRACT

An infant monitoring device includes a sensor connected to an alarm for alerting a parent when an infant is in a predetermined position. In a second embodiment, the alarm is activated only if the same body position is detected by the sensor for the duration of a delay determined by a timer. In a third embodiment, a wireless transmitter is connected to the sensor for communicating with a wireless receiver and activating a remote alarm. In a fourth embodiment, a timer is connected between the sensor and the wireless transmitter to reduce false alarms. In a fifth embodiment, a plurality of sensors are connected to a multi-channel wireless transmitter for sensing a plurality of positions, and communicating with a multi-channel wireless receiver for activating a remote alarm. In a sixth embodiment, a timer is connected between the sensors and the multi-channel transmitter for reducing false alarms. In all embodiments, the sensor may be a disc-shaped or spherical mercury switch with one or more pairs of electrodes for detecting one or a plurality of positions, or the sensor may be a hollow housing with a pendulum arm making contact with electrodes on the interior thereof.

10 Claims, 3 Drawing Sheets

INFANT MONITORING DEVICE

BACKGROUND OF THE INVENTION

1. Field of the Invention

This invention relates generally to infant monitoring devices.

2. Prior Art

Many parents wish to monitor their infant child's condition when they are separated from the child, for example, by being in another room, and they cannot see or readily hear the child. Information about the child's position and movements is very useful. For example, rapid movements may indicate restlessness; frequent shifting and turning may indicate a rash, fever, dirty diaper, etc.; an upright position may indicate that the child is awake and is attempting to climb out of its crib; prolonged sleeping in the prone position may lead to an increased risk of sudden infant death syndrome (SIDS), which is associated with such a position; and prolonged sleeping in the supine position may lead to an increased risk of choking on vomit or developing a flattened head.

Although radio frequency infant listening devices are available, they only provide a one-way audio link between the child and the parent. They cannot provide information about the child's status, such as its sleeping position, whether it is asleep or awake, or its movements when awake.

Various sleep posture monitoring and warning systems have also been proposed. U.S. Pat. No. 4,617,525 to Lloyd discloses a device with a sleep position sensor that activates an alarm after a predetermined delay set by a timer. The sensor also sends its signal to a recording device through a transmitter and a receiver. The transmitter and receiver are connected by a cable, so that the device is inconvenient to use. Further, spurious signals may be sent by the transmitter. U.S. Pat. No. 5,038,137 to Lloyd discloses a device with a plurality of mercury switches for detecting different sleeping positions. It cannot prevent serious injury or death because it may fail to wake the sleeping person with its audible alarm, for example, if an infant is suffocating or is about to die of SID, and there is no one nearby to hear the alarm and revive the infant. U.S. Pat. No. 5,081,447 to Echols discloses a sleep position alarm with a plurality of head-mounted sensors for alerting the person when he or she is sleeping supine, so as to encourage sleeping on a side. It is not suitable for use as a SID warning device, because it cannot detect the prone position. Further, it must be worn on the head, which is uncomfortable.

Some prior art warning devices use a single mercury switch for detecting a single position, and others use a plurality of mercury switches for detecting different positions. Some switches comprise straight tubes with a pair of electrodes at one end, and a drop of mercury that slosh between the ends of the tube. Other switches have angular internal contours. The straight or angular paths defined by prior art switches tend to provide unreliable sensing, and therefore cause false alarms and provide erroneous positional information.

OBJECTS OF THE INVENTION

Accordingly an object of the present invention is to provide an infant monitoring device that provides positional information about an infant.

Another object of the present invention is to provide an infant monitoring device that alerts parents when the infant is in a potentially dangerous position.

Another object of the present invention is to provide an infant monitoring device that alerts parents even when they are visually and audibly separated from the infant.

Another object of the present invention is to provide an infant monitoring device that provides accurate positional information.

Yet another object of the present invention is to provide an infant monitoring device that is convenient to set up and use.

Further objects of the present invention will become apparent from a consideration of the drawings and ensuing description.

BRIEF SUMMARY OF THE INVENTION

An infant monitoring device includes a sensor connected to an alarm for alerting an adult when the infant is in a predetermined position. In a second embodiment, a timer is connected between the sensor and the alarm for activating the alarm after a delay to reduce false alarms. In a third embodiment, a wireless transmitter is connected to the sensor for activating a remote alarm with a wireless receiver. In a fourth embodiment, a timer is connected between the sensor and the wireless transmitter to reduce false alarms. In a fifth embodiment, a plurality of sensors are connected to a multi-channel wireless transmitter for sensing a plurality of positions and transmitting such information to a multi-channel wireless receiver for activating a remote alarm. In a sixth embodiment, a timer is connected between the sensors and the multi-channel transmitter for reducing false alarms. In all embodiments, the sensor may be a disc-shaped or spherical mercury switch with one or more pairs of electrodes for detecting one or a plurality of positions.

DETAILED DESCRIPTION OF THE INVENTION

Figure 1:
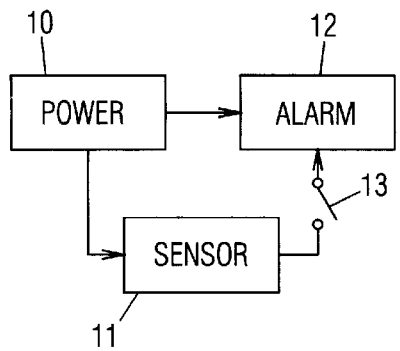
FIG. 1 is a schematic diagram of an infant monitoring device in accordance with a first embodiment of the invention.

FIG. 1:

In accordance with a first embodiment of the invention shown in the schematic diagram of FIG. 1, an infant monitoring device includes a power supply 10, such as a battery or AC adapter, powering a body position sensor 11 and an alarm 12. An on/off switch 13 enables or disables alarm 12, which may be an audible alarm, a flashing light, etc. Sensor 11 is attached to an infant, for example, to its clothing, and is oriented for detecting a predetermined body position, for example, a prone position that may lead to SID. When such a position is detected, alarm 12 is activated to alert a nearby adult to take appropriate action.

Figure 2:
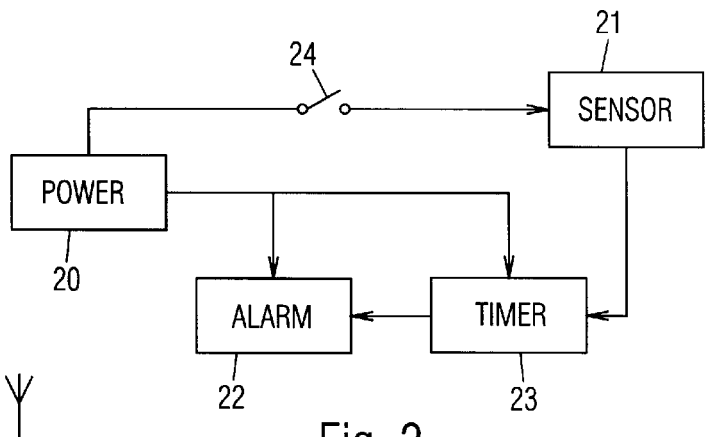
FIG. 2 is a schematic diagram of an infant monitoring device in accordance with a second embodiment of the invention.

FIG. 2: In accordance with a second embodiment of the invention shown in the schematic diagram of FIG. 2, an infant monitoring device includes a power supply 20 powering a body position sensor 21, an alarm 22, and a timer 23. An on/off switch 24 enables or disables sensor 21. Timer 23 is connected between sensor 21 and alarm 22. When a predetermined position is detected by sensor 21, for example, a position that may lead to a flattened head, timer 23 is activated. If the input from sensor 21 is uninterrupted for the duration of the delay, which indicates that the infant is remaining in the same position, alarm 22 is activated by timer 23. If the input from sensor 21 is interrupted, which indicates that the infant has changed position, timer 23 is reset, so that alarm 22 is not activated. Thus timer 23 prevents false alerts by activating alarm 22 only if the infant has remained in the same position for a predetermined time. This is particularly useful for preventing SID and flattened heads.

Figure 3:
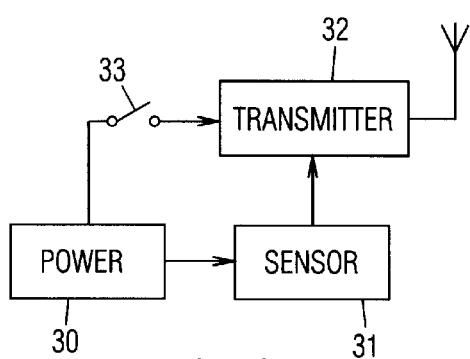
FIG. 3 is a schematic diagram of a transmitter of an infant monitoring device in accordance with a third embodiment of the invention.
Figure 5:
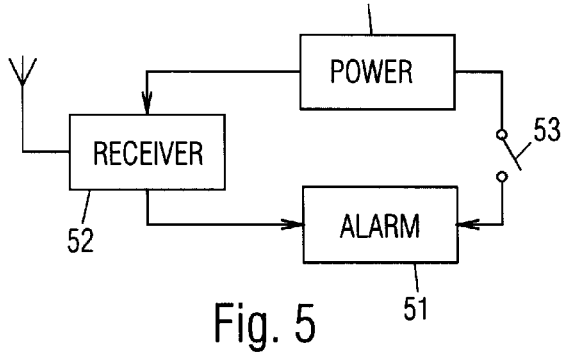
FIG. 5 is a schematic diagram of a receiver of an infant monitoring device for the third and fourth embodiments of the invention.

FIG. 3:

In accordance with a third embodiment of the invention shown in the schematic diagram of FIG. 3, an infant monitoring device includes a power supply 30 powering a body position sensor 31 and a wireless transmitter 32 for activating a remote alarm described in conjunction with FIG. 5. An on/off switch 33 enables or disables transmitter 32, which may be a radio frequency, infrared, or other suitable transmitter.

Figure 4:
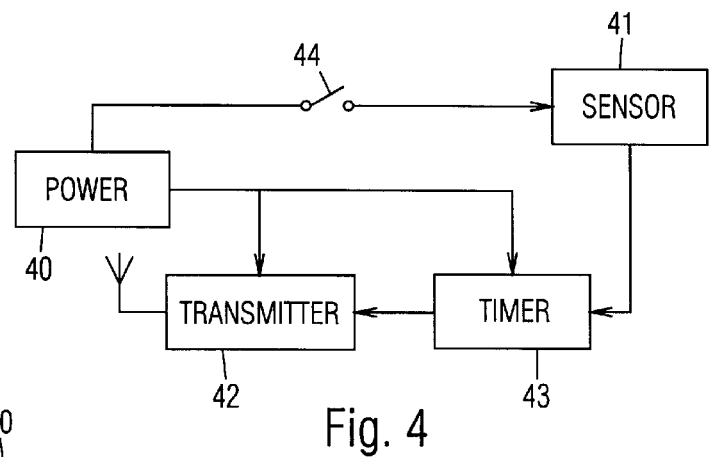
FIG. 4 is a schematic diagram of a transmitter of an infant monitoring device in accordance with a fourth embodiment of the invention.

FIG. 4:

In accordance with a fourth embodiment of the invention shown in the schematic diagram of FIG. 4, an infant monitoring device includes a power supply 40 powering a body position sensor 41, a wireless transmitter 42, and a timer 43. Timer 43 is connected between sensor 41 and transmitter 42. An on/off switch 44 enables or disables sensor 41. Transmitter 42 is activated only if the same body position is sensed by position sensor 41 for the duration of a delay determined by timer 43. Transmitter 42, which may be a radio frequency, infrared, or other suitable transmitter, is arranged for activating a remote alarm described in conjunction with FIG. 5.

FIG. 5:

As shown in FIG. 5, a power supply 50 is connected to an alarm 51 and a wireless receiver 52. An on/off switch 53 enables or disables alarm 51. Receiver 52, which may be a radio frequency, infrared, or other suitable receiver, is arranged for receiving the signal from the transmitter of FIGS. 3 or 4 for activating alarm 51. Alarm 51 may thus be located at a remote position from the infant, such as in a separate room or even in a separate building, and may also be made portable so that the infant can be monitored by a roaming adult. The wireless connection between the transmitter and receiver enables the infant monitoring device to be easily set up and used.

Figure 6:
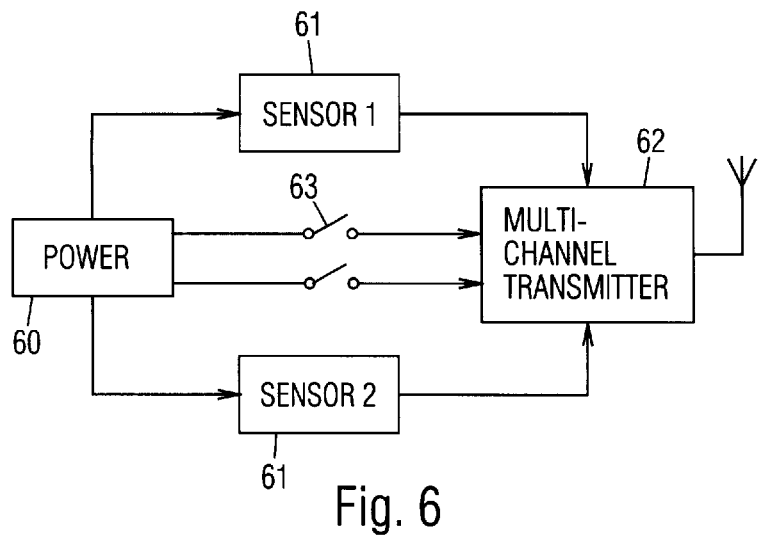
FIG. 6 is a schematic diagram of a transmitter of an infant monitoring device in accordance with a fifth embodiment of the invention.

FIG. 6:

In accordance with a fifth embodiment of the invention shown in the schematic diagram of FIG. 6, an infant monitoring device includes a power supply 60 powering a plurality of body position sensors 61, and a wireless multi-channel transmitter 62. On/off switches 63 selectively enable or disable each channel of transmitter 62. Sensors 61 are arranged for detecting different body positions. The detected positions are broadcast by transmitter 62 on different channels. Transmitter 62, which may be a radio frequency, infrared, or other suitable transmitter, is arranged for activating a remote alarm described in conjunction with FIG. 8.

Figure 7:
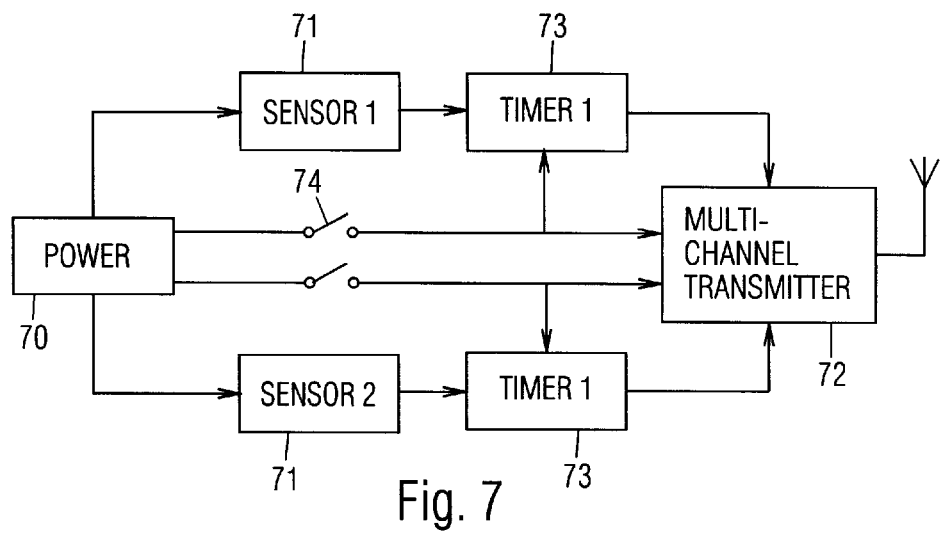
FIG. 7 is a schematic diagram of a transmitter of an infant monitoring device in accordance with a sixth embodiment of the invention.

FIG. 7:

In accordance with a sixth embodiment of the invention shown in the schematic diagram of FIG. 7, an infant monitoring device includes a power supply 70 powering a plurality of body position sensors 71, a wireless multi-channel transmitter 72, and a plurality of timers 73. Timers 73 are connected between sensors 71 and transmitter 72. On/off switches 74 selectively enable or disable the channels of transmitter 72. Transmitter 72 is activated only if the same body position is sensed by one of position sensors 71 for the duration of a delay determined by a corresponding timer 73. Sensors 71 are arranged for detecting different body positions. The detected positions are broadcast by transmitter 72 on different channels. Transmitter 72, which may be a radio frequency, infrared, or other suitable transmitter, is arranged for activating a remote alarm described in conjunction with FIG. 8.

Figure 8:
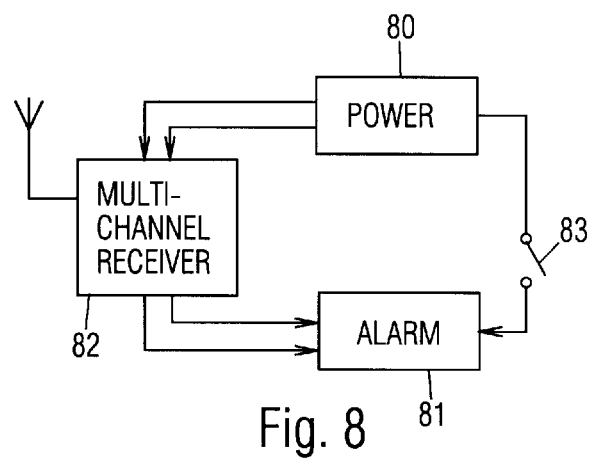
FIG. 8 is a schematic diagram of a receiver of an infant monitoring device for the fifth and sixth embodiments of the invention.

FIG. 8:

As shown in FIG. 8, a power supply 80 is connected to an alarm 81 and a wireless multi-channel receiver 82. An on/off switch 83 enables or disables alarm 81. Receiver 82, which may be a radio frequency, infrared, or other suitable receiver, is arranged for receiving the signal from the transmitter of FIGS. 6 or 7 for activating alarm 81. Alarm 81 may thus be located at a remote position from the infant, such as in a separate room or even in a separate building, and may also be made portable so that the infant can be monitored by a roaming adult. The wireless connection between the transmitter and receiver enables the infant monitoring device to be easily set up and used.

Figure 9:
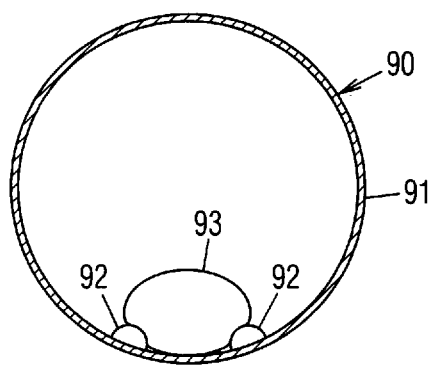
FIG. 9 is a first embodiment of a positional sensor of the infant monitoring device.

FIG. 9:

A sensor 90 is shown in FIG. 9. Sensor 90 may be used as the sensor in all of the embodiments of the present invention. Sensor 90 includes a hollow disc-shaped or spherical housing 91 with a pair of electrodes 92 arranged on the interior thereof. Electrodes 92 are connected by a drop of mercury 93 when sensor 90 is oriented in a predetermined position. The smooth, round contour of housing 91 provides more reliable position sensing.

Figure 10:
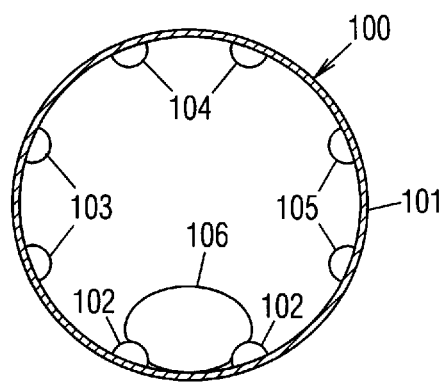
FIG. 10 is a second embodiment of the positional sensor of the infant monitoring device.

FIG. 10:

An alternative sensor 100 is shown in FIG. 10. Sensor 100 may also be used as the sensor in all of the embodiments of the present invention. A single sensor 100 provides the functionality of the plurality of sensors in the embodiments shown in FIGS. 6 and 7. Sensor 100 includes a hollow disc-shaped or spherical housing 101 with a plurality of pairs of electrodes 102–105 arranged radially around the interior thereof. The electrodes may be arranged evenly around the interior of a sphere for detecting positions in three axes. Each pair of electrodes is connected by a connecting means or drop of mercury 106 when sensor 100 is oriented in a corresponding position. The round contour of housing 101 enables mercury 106 to roll smoothly from one pair of electrodes to another, so that it provides more reliable position sensing.

Figure 11:
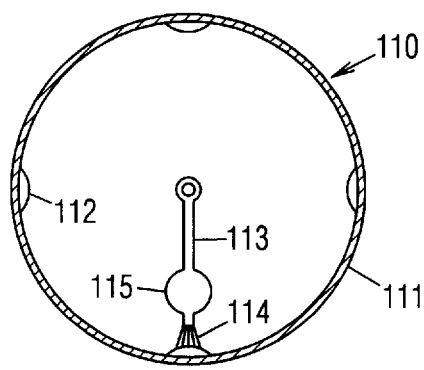
FIG. 11 is a third embodiment of the positional sensor of the infant monitoring device.

FIG. 11:

Still another alternative sensor 110 is shown in FIG. 11. Sensor 110 may also be used as the sensor in all of the embodiments of the present invention. A single sensor 110 provides the functionality of the plurality of sensors in the embodiments shown in FIGS. 6 and 7. Sensor 110 includes a hollow disc-shaped or spherical housing 111 with a plurality of electrodes 112 arranged radially around the interior thereof. The electrodes may be arranged evenly around the interior of a sphere for detecting positions in three axes. A connecting means or conductive pendulum arm 113 with a conductive brush 114 at a distal end is weighed down with a weight 115 adjacent the same end. Brush 114 makes electrical contact with electrodes 112 as housing 111 rotates beneath it. Being pivoted for smooth rotation, arm 113 provides more reliable position sensing.

Figure 12:
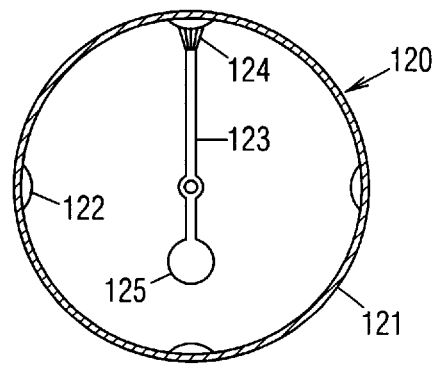
FIG. 12 is a fourth embodiment of the positional sensor of the infant monitoring device.

FIG. 12:

Yet another alternative sensor 120 is shown in FIG. 12. Sensor 120 may also be used as the sensor in all of the embodiments of the present invention. A single sensor 120 provides the functionality of the plurality of sensors in the embodiments shown in FIGS. 6 and 7. Sensor 120 includes a hollow disc-shaped or spherical housing 121 with a plurality of electrodes 122 arranged radially around the interior thereof. The electrodes may be arranged evenly around the interior of a sphere for detecting positions in three axes. A connecting means or conductive pendulum arm 123 with a conductive brush 124 at one end is weighed down at an opposite end with a weight 125. Brush 124 makes electrical contact with electrodes 122 as housing 121 rotates above it. Being pivoted for smooth rotation, arm 123 provides more reliable position sensing.

Figure 13:
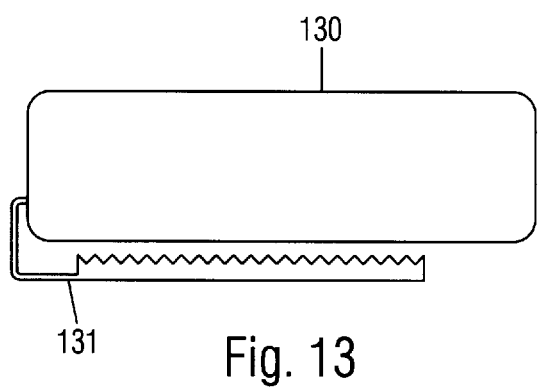
FIG. 13 is a side view of a transmitter housing of the infant monitoring device.

FIG. 13:

As shown in the side view in FIG. 13, the embodiments shown in FIGS. 1–4, and 6–7 may be received in a housing 130 with a spring clip 131 for attaching to an infant's clothing. For proper sensing, housing 130 should be consistently attached to the same location on the infant, such as on the front of a diaper, and oriented in the same position at all times.

SUMMARY AND SCOPE

Accordingly, I have provided an infant monitoring device that provides positional information about an infant. It alerts parents when the infant is in a potentially dangerous position. It alerts parents even when they are visually and audibly separated from the infant. It provides accurate positional information, and it is convenient to set up and use.

Although the above descriptions are specific, they should not be considered as limitations on the scope of the invention, but only as examples of the embodiments. Many substitutes and variations are possible within the teachings of the invention. For example, the sensor may be arranged for detecting a variety of different body positions. The timer may be fixed or adjustable. More sensors may be provided for detecting more positions, and the transmitter and receiver may include additional channels for communicating the additional information. A plurality of distinct alarms may be provided, for example, different sounds or lights, for indicating different body positions. The monitoring may be used on adults. Therefore, the scope of the invention should be determined by the appended claims and their legal equivalents, not by the examples given.

I claim:

1. A body position monitoring device, comprising:

a sensor for attaching to a person for detecting a predetermined body position, said sensor comprising a hollow housing with a circular interior surface, an electrode means attached to said circular interior surface, and a connecting means positioned on said circular interior surface and freely movable completely around a circumference thereof, said connecting means generally remaining in a single radial position regardless of a radial orientation of said housing, said connecting means making contact with said electrode means only when said housing is rotated such that said electrode means is generally in said single radial position, said single radial position corresponding to said predetermined body position, said connecting means disengaging from said electrode means when said housing is rotated to other positions; and an alarm connected to said sensor for producing an alert when said predetermined body position is detected.

2. The body position monitoring device of claim 1, wherein said electrode means comprises a spaced apart pair of electrodes, and said connecting means comprises a drop of mercury sized for spanning said pair of electrodes.

3. The body position monitoring device of claim 1, wherein said connecting means comprises a conductive pendulum arm pivoting about a center of said housing, a distal end of said pendulum arm making contact with said electrode means on said circular interior surface.

4. The body position monitoring device of claim 1, wherein said housing comprises a spherical housing for detecting said body position around three axes.

5. The body position monitoring device of claim 1, further including a plurality of electrode means arranged on said circular interior surface of said housing in radial positions about a center thereof for detecting a plurality of different body positions.

6. A body position monitoring device, comprising:

a sensor for attaching to a person for detecting a predetermined body position, said sensor comprising a hollow housing with a circular interior surface, an electrode means attached to said circular interior surface, and a connecting means positioned on said circular interior surface and freely movable completely around a circumference thereof, said connecting means generally remaining in a single radial position regardless of a radial orientation of said housing, said connecting means making contact with said electrode means only when said housing is rotated such that said electrode means is generally in said single radial position, said single radial position corresponding to said predetermined body position, said connecting means disengaging from said electrode means when said housing is rotated to other positions;

a wireless transmitter connected to said sensor and arranged to transmit only when said body position is detected;

a wireless receiver communicating wirelessly with said transmitter, said wireless receiver for being located away from said person; and an alarm connected to said wireless receiver for producing an alert when said body position is detected.

7. The body position monitoring device of claim 6, wherein said electrode means comprise a pair of spaced apart electrodes, and said connecting means comprises a drop of mercury.

8. The body position monitoring device of claim 6, wherein said connecting means comprises a conductive pendulum arm pivoted about a center of said housing, a distal end of said pendulum arm making contact with said electrode means on said circular interior surface.

9. The body position monitoring device of claim 6, wherein said housing comprises a spherical housing for detecting said body position around three axes.

10. The body position monitoring device of claim 6, wherein said transmitter comprises a multi-channel transmitter, and said receiver comprises a multi-channel receiver.

* * * * *